(12) United States Patent
Phillips et al.

(10) Patent No.: US 12,154,321 B2
(45) Date of Patent: Nov. 26, 2024

(54) STRUCTURED REPRESENTATIONS FOR INTERPRETABLE MACHINE LEARNING APPLICATIONS IN MEDICAL IMAGING

(71) Applicant: ELUCID BIOIMAGING INC., Boston, MA (US)

(72) Inventors: Matthew Phillips, Apex, NC (US); Andrew J. Buckler, Boston, MA (US)

(73) Assignee: ELUCID BIOIMAGING INC., Boston, MA (US)

( * ) Notice: Subject to any disclaimer, the term of this patent is extended or adjusted under 35 U.S.C. 154(b) by 0 days.

(21) Appl. No.: 18/504,769

(22) Filed: Nov. 8, 2023

(65) Prior Publication Data

US 2024/0153252 A1  May 9, 2024

Related U.S. Application Data

(60) Provisional application No. 63/424,098, filed on Nov. 9, 2022.

(51) Int. Cl.
| | |
|---|---|
| *G06V 10/774* | (2022.01) |
| *A61B 5/024* | (2006.01) |
| *G06T 7/00* | (2017.01) |
| *G06T 7/73* | (2017.01) |
| *G06V 20/70* | (2022.01) |
| *G16H 50/50* | (2018.01) |

(52) U.S. Cl.
CPC ............ *G06V 10/774* (2022.01); *A61B 5/024* (2013.01); *G06T 7/0012* (2013.01); *G06T 7/73* (2017.01); *G06V 20/70* (2022.01); *G16H 50/50* (2018.01); *G06T 2207/20081* (2013.01); *G06T 2207/30016* (2013.01); *G06T 2207/30048* (2013.01); *G06T 2207/30104* (2013.01); *G06V 2201/03* (2022.01)

(58) Field of Classification Search
CPC .. G06V 10/774; G06V 20/70; G06V 2201/03; G06V 10/772; G06V 40/14; G06V 10/426; A61B 5/024; G06T 7/0012; G06T 7/73; G06T 2207/20081; G06T 2207/30016; G06T 2207/30048; G06T 2207/30104; G16H 50/50; G16H 30/40; G16H 50/20
See application file for complete search history.

(56) References Cited

U.S. PATENT DOCUMENTS

| | | |
|---|---|---|
| 10,813,612 B2 | 10/2020 | Min |
| 11,501,436 B2 | 11/2022 | Min et al. |
| 2015/0254418 A1 | 9/2015 | Sankaran et al. |

(Continued)

OTHER PUBLICATIONS

Tonino, P.A., et al., Fractional flow reserve versus angiography for guiding percutaneous coronary intervention. N Engl J Med, 2009. 360(3): p. 213-24.

(Continued)

*Primary Examiner* — Siamak Harandi
(74) *Attorney, Agent, or Firm* — PEARL COHEN ZEDEK LATZER BARATZ LLP

(57) ABSTRACT

Systems and method can be provided to transform input data (e.g., CT imaging data) into structured representations to create interpretable models. Another aspect of the current invention can be generating labels synthetically to apply to real data according to a biologically-based labelling technique to guide the model training with a priori mechanistic knowledge.

28 Claims, 18 Drawing Sheets

(56) References Cited

U.S. PATENT DOCUMENTS

| | | | |
|---|---|---|---|
| 2019/0074082 | A1 | 3/2019 | Buckler et al. |
| 2020/0356864 | A1* | 11/2020 | Neumann ............... G06N 3/088 |
| 2021/0166785 | A1 | 6/2021 | Yip et al. |
| 2021/0319558 | A1* | 10/2021 | Min ...................... A61K 49/04 |
| 2021/0334962 | A1 | 10/2021 | Min et al. |
| 2021/0366114 | A1 | 11/2021 | Min et al. |
| 2022/0237781 | A1 | 7/2022 | Panda et al. |
| 2022/0386979 | A1 | 12/2022 | Min et al. |
| 2022/0392065 | A1 | 12/2022 | Min et al. |
| 2023/0005582 | A1* | 1/2023 | Buckler ................. G16H 50/50 |
| 2023/0132940 | A1 | 5/2023 | Min et al. |
| 2023/0289963 | A1 | 9/2023 | Min et al. |

OTHER PUBLICATIONS

De Bruyne, B., et al., Fractional flow reserve-guided PCI for stable coronary artery disease. N Engl J Med, 2014. 371(13): p. 1208-17.

Pijls, N.H., et al., Fractional flow reserve versus angiography for guiding percutaneous coronary intervention in patients with multivessel coronary artery disease: 2-year follow-up of the FAME (Fractional Flow Reserve Versus Angiography for Multivessel Evaluation) study. J Am Coll Cardiol, 2010. 56(3): p. 177-84.

Collet, C., et al., Coronary computed tomography angiography for heart team decision-making in multivessel coronary artery disease—Syntax III. ESC, 2018. 2018(0): p. 10.

Chalkidou, A., et al., HeartFlow Technical Evaluation. 2015, KiTEC—King's Technology Evaluation Centre.

Kishi, S., et al., Fractional Flow Reserve Estimated at Coronary CT Angiography in Intermediate Lesions: Comparison of Diagnostic Accuracy of Different Methods to Determine Coronary Flow Distribution. Radiology, 2018. 287(1): p. 76-84.

Min, J.K., Y. Chandrashekhar, and J. Narula, Noninvasive FFRCT After STEMI: Looking for the Guilty Bystander. JACC Cardiovasc Imaging, 2017. 10(4): p. 500-502.

Liu, R., et al., [Noninvasive numerical simulation of coronary fractional flow reserve based on lattice Boltzmann method]. Sheng Wu Yi Xue Gong Cheng Xue Za Zhi, 2018. 35(3): p. 384-389.

Giannopoulos, A.A., et al., Diagnostic performance of a Lattice Boltzmann-based method for CT-based fractional flow reserve. EuroIntervention, 2018. 13(14): p. 1696-1704.

Members, W.C., et al., 2021 AHA/ACC/ASE/Chest/SAEM/SCCT/SCMR guideline for the evaluation and diagnosis of chest pain: a report of the American College of Cardiology/American Heart Association Joint Committee on Clinical Practice Guidelines. Journal of the American College of Cardiology, 2021. 78(22): p. e187-e285.

Ahmadi, A., et al., Lesion-Specific and Vessel-Related Determinants of Fractional Flow Reserve Beyond Coronary Artery Stenosis. JACC Cardiovasc Imaging, 2018. 11(4): p. 521-530.

Ahmadi, A., et al., Association of Coronary Stenosis and Plaque Morphology With Fractional Flow Reserve and Outcomes. JAMA Cardiol, 2016. 1(3): p. 350-7.

Narula, J., et al., Histopathologic characteristics of atherosclerotic coronary disease and implications of the findings for the invasive and noninvasive detection of vulnerable plaques. J Am Coll Cardiol, 2013. 61(10): p. 1041-51.

Baumann, S., et al., Association of Serum Lipid Profile With Coronary Computed Tomographic Angiography-derived Morphologic and Functional Quantitative Plaque Markers. J Thorac Imaging, 2019. 34(1): p. 26-32.

Glagov, S., et al., Compensatory enlargement of human atherosclerotic coronary arteries. N Engl J Med, 1987. 316(22): p. 1371-5.

Ahmadi, A., A. Kini, and J. Narula, Discordance between ischemia and stenosis, or PINSS and NIPSS: are we ready for new vocabulary? JACC Cardiovasc Imaging, 2015. 8(1): p. 111-114.

Lavi, S., et al., Segmental coronary endothelial dysfunction in patients with minimal atherosclerosis is associated with necrotic core plaques. Heart, 2009. 95(18): p. 1525-1530.

Tesche, C., et al., Coronary CT Angiography-derived Fractional Flow Reserve: Machine Learning Algorithm versus Computational Fluid Dynamics Modeling. Radiology, 2018. 288(1): p. 64-72.

Coenen, A., et al., Diagnostic Accuracy of a Machine-Learning Approach to Coronary Computed Tomographic Angiography-Based Fractional Flow Reserve: Result From the Machine Consortium. Circ Cardiovasc Imaging, 2018. 11(6): p. e007217.

Diaz-Zamudio, M., et al., Automated Quantitative Plaque Burden from Coronary CT Angiography Noninvasively Predicts Hemodynamic Significance by using Fractional Flow Reserve in Intermediate Coronary Lesions. Radiology, 2015. 276(2): p. 408-15.

Tesche, C., et al., Influence of Coronary Calcium on Diagnostic Performance of Machine Learning CT-FFR: Results From Machine Registry. JACC Cardiovasc Imaging, 2020. 13(3): p. 760-770.

Kolossváry, M., et al., Radiomic Features Are Superior to Conventional Quantitative Computed Tomographic Metrics to Identify Coronary Plaques With Napkin-Ring Sign. Circ Cardiovasc Imaging, 2017. 10(12).

Dey, D. and F. Commandeur, Radiomics to Identify High-Risk Atherosclerotic Plaque From Computed Tomography: The Power of Quantification. Circ Cardiovasc Imaging, 2017. 10(12).

Dey, D., et al., Automated three-dimensional quantification of noncalcified coronary plaque from coronary CT angiography: comparison with intravascular US. Radiology, 2010. 257(2): p. 516-22.

Beam, A.L. and I.S. Kohane, Translating artificial intelligence into clinical care. Jama, 2016. 316(22): p. 2368-2369.

Lecun, Y., Y. Bengio, and G. Hinton, Deep learning. nature, 2015. 521(7553): p. 436.

Hertz, J., A. Krogh, and R.G. Palmer, Introduction to the theory of neural computation. 1991: Addison-Wesley/Addison Wesley Longman.

Bishop, C. and C.M. Bishop, Neural networks for pattern recognition. 1995: Oxford University press.

Lee, T.S. and D. Mumford, Hierarchical Bayesian inference in the visual cortex. JOSA A, 2003. 20(7): p. 1434-1448.

Lee, T.S., et al., The role of the primary visual cortex in higher level vision. Vision research, 1998. 38(15-16): p. 2429-2454.

Krizhevsky, A., I. Sutskever, and G.E. Hinton. Imagenet classification with deep convolutional neural networks. in Advances in neural information processing systems. 2012.

Dosovitskiy, A., et al., An image is worth 16x16 words: Transformers for image recognition at scale. arXiv preprint arXiv:2010.11929, 2020.

Lecun, Y., et al., Gradient-based learning applied to document recognition. Proceedings of the IEEE, 1998. 86(11): p. 2278-2324.

Mikolov, T., et al. Strategies for training large scale neural network language models. in Automatic Speech Recognition and Understanding (ASRU), 2011 IEEE Workshop on. 2011. IEEE.

Collobert, R., et al., Natural language processing (almost) from scratch. Journal of Machine Learning Research, 2011. 12(Aug): p. 2493-2537.

Wong, T.Y. and N.M. Bressler, Artificial intelligence with deep learning technology looks into diabetic retinopathy screening. Jama, 2016. 316(22): p. 2366-2367.

Syafiandini, A.F., et al. Identification of gene expression linked to malignancy of human colorectal carcinoma using restricted Boltzmann machines. in Proceedings of the 7th International Conference on Bioscience, Biochemistry and Bioinformatics. 2017. ACM.

Gunawardena, T., et al., Endothelial Dysfunction and Coronary Vasoreactivity—A Review of the History, Physiology, Diagnostic Techniques, and Clinical Relevance. Curr Cardiol Rev, 2021. 17(1): p. 85-100.

Ramanlal, R. and V. Gupta, Physiology, Vasodilation, in StatPearls. 2022: Treasure Island (FL).

Hellsten, Y., et al., Vasodilator interactions in skeletal muscle blood flow regulation. J Physiol, 2012. 590(24): p. 6297-305.

Webb, R.C., Smooth muscle contraction and relaxation. Adv Physiol Educ, 2003. 27(1-4): p. 201-6.

Ahmadi, A., A. Kini, and J. Narula, Discordance between ischemia and stenosis, or PINSS and NIPSS: are we ready for new vocabulary? 2015, JACC: Cardiovascular Imaging.

(56) References Cited

OTHER PUBLICATIONS

Lavi, S., et al., The interaction between coronary endothelial dysfunction, local oxidative stress, and endogenous nitric oxide in humans. Hypertension, 2008. 51(1): p. 127-133.
Wilson, C., M.D. Lee, and J.G. McCarron, Acetylcholine released by endothelial cells facilitates flow-mediated dilatation. The Journal of physiology, 2016. 594(24): p. 7267-7307.
Buckler, A.J., et al., Virtual Transcriptomics: Noninvasive Phenotyping of Atherosclerosis by Decoding Plaque Biology From Computed Tomography Angiography Imaging. Arterioscler Thromb Vasc Biol, 2021. 41(5): p. 1738-1750.
Rangel-Castilla, L., et al., Cerebral pressure autoregulation in traumatic brain injury. Neurosurg Focus, 2008. 25(4): p. E7.
Irvin, J., et al. Chexpert: A large chest radiograph dataset with uncertainty labels and expert comparison. in Proceedings of the AAAI conference on artificial intelligence. 2019.
Adebayo, J., et al., Sanity checks for saliency maps. Advances in neural information processing systems, 2018. 31.
Springenberg, J.T., et al., Striving for simplicity: The all convolutional net. arXiv preprint arXiv:1412.6806, 2014.
Rudin, C., Stop explaining black box machine learning models for high stakes decisions and use interpretable models instead. Nature Machine Intelligence, 2019. 1(5): p. 206-215.
Ghassemi, M., L. Oakden-Rayner, and A.L. Beam, The false hope of current approaches to explainable artificial intelligence in health care. The Lancet Digital Health, 2021. 3(11): p. e745-e750.
Rudin, C., et al., Interpretable machine learning: Fundamental principles and 10 grand challenges. Statistics Surveys, 2022. 16: p. 1-85.
Li, O., et al. Deep learning for case-based reasoning through prototypes: A neural network that explains its predictions. in Proceedings of the AAAI Conference on Artificial Intelligence. 2018.
Lucieri, A., et al., Achievements and challenges in explaining deep learning based computer-aided diagnosis systems. arXiv preprint arXiv:2011.13169, 2020.
Varga-Szemes, A., et al., Coronary plaque assessment of Vasodilative capacity by CT angiography effectively estimates fractional flow reserve. Int J Cardiol, 2021.
Sheahan, M., et al., Atherosclerotic Plaque Tissue: Noninvasive Quantitative Assessment of Characteristics with Software-aided Measurements from Conventional CT Angiography. Radiology, 2018. 286(2): p. 622-631.
Shorten, C. and T.M. Khoshgoftaar, A survey on image data augmentation for deep learning. Journal of big data, 2019. 6(1): p. 1-48.
Zhang, H., et al., mixup: Beyond empirical risk minimization. arXiv preprint arXiv:1710.09412, 2017.
Ronneberger, O., P. Fischer, and T. Brox. U-net: Convolutional networks for biomedical image segmentation. in International Conference on Medical image computing and computer-assisted intervention. 2015. Springer.
Abbaszadegan, M.R., et al., Automated detection of prevalent mutations in BRCA1 and BRCA2 genes, using a fluorogenic PCR allelic discrimination assay. Genet Test, 1997. 1(3): p. 171-80.
Collet, C., et al., Measurement of hyperemic pullback pressure gradients to characterize patterns of coronary atherosclerosis. Journal of the American College of Cardiology, 2019. 74(14): p. 1772-1784.
Zeiler, M.D. and R. Fergus. Visualizing and understanding convolutional networks. in European conference on computer vision. 2014. Springer.
Krizhevsky, A., I. Sutskever, and G.E. Hinton, Imagenet classification with deep convolutional neural networks. Communications of the ACM, 2017. 60(6): p. 84-90.
Hua, X., et al., Optimizing power to track brain degeneration in Alzheimer's disease and mild cognitive impairment with tensor-based morphometry: an ADNI study of 515 subjects. Neuroimage, 2009. 48(4): p. 668-81.
Van Klaveren, R.J., et al., Management of lung nodules detected by volume CT scanning. N Engl J Med, 2009. 361(23): p. 2221-9.
Wahl, R.L., et al., From RECIST to PERCIST: evolving considerations for PET response criteria in solid tumors. Journal of Nuclear Medicine, 2009. 50(Suppl 1): p. 122S-150S.
Bhooshan, N., et al., Cancerous breast lesions on dynamic contrast-enhanced MR images: computerized characterization for image-based prognostic markers. Radiology, 2010. 254(3): p. 680-90.
Fuleihan, G.E.H., et al., Reproducibility of DXA absorptiometry: a model for bone loss estimates. Journal of Bone and Mineral Research, 1995. 10(7): p. 1004-1014.
Sargent, D., et al., Validation of novel imaging methodologies for use as cancer clinical trial end-points. European Journal of Cancer, 2009. 45(2): p. 290-299.
Sonck, J., et al., Motorized fractional flow reserve pullback: accuracy and reproducibility. Catheterization and Cardiovascular Interventions, 2020. 96(3): p. E230-E237.
Pijls, N.H., et al., Measurement of fractional flow reserve to assess the functional severity of coronary-artery stenoses. N Engl J Med, 1996. 334(26): p. 1703-8.
Çiçek, Ö., et al. 3D U-Net: learning dense volumetric segmentation from sparse annotation. in International conference on medical image computing and computer-assisted intervention. 2016. Springer.
International Search Report and Written Opinion for PCT Application No. PCT/US23/79184 dated Apr. 4, 2024.

* cited by examiner

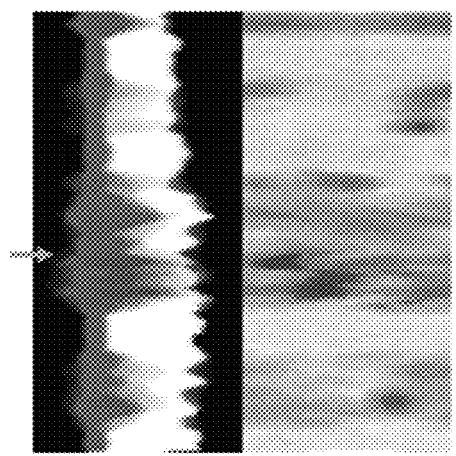
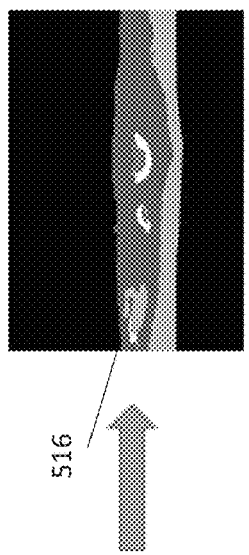
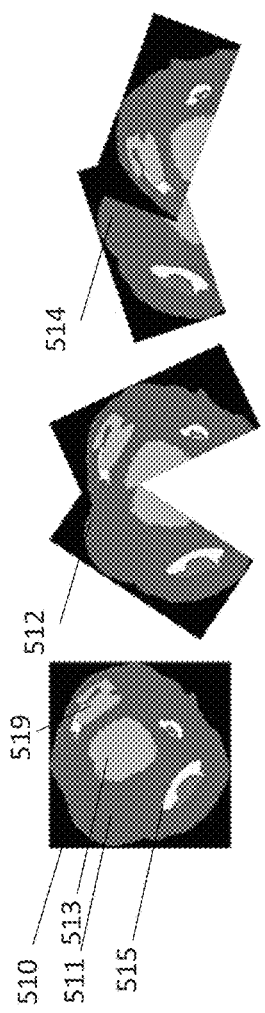
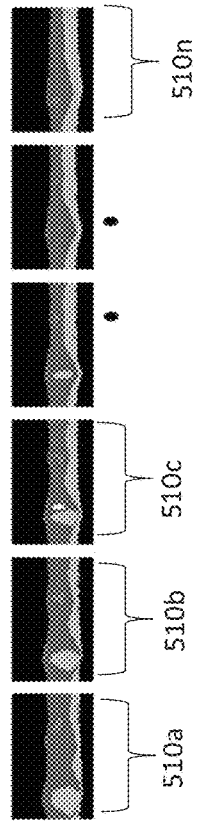
Figure 5A
Figure 5B
Figure 5C
Figure 5D
Figure 5E

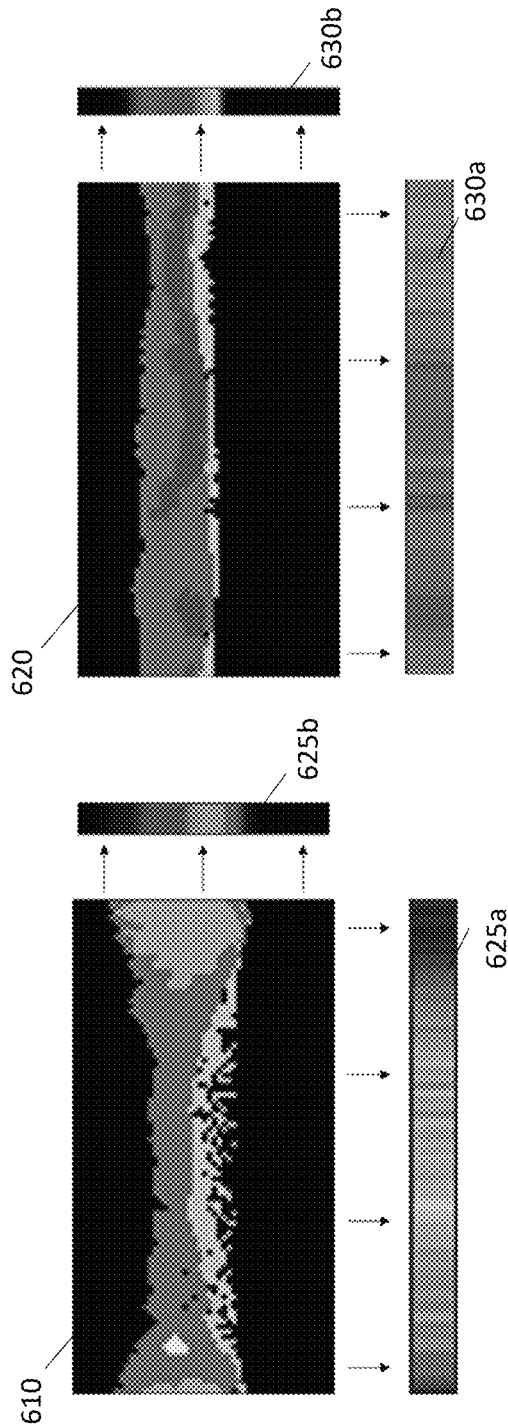
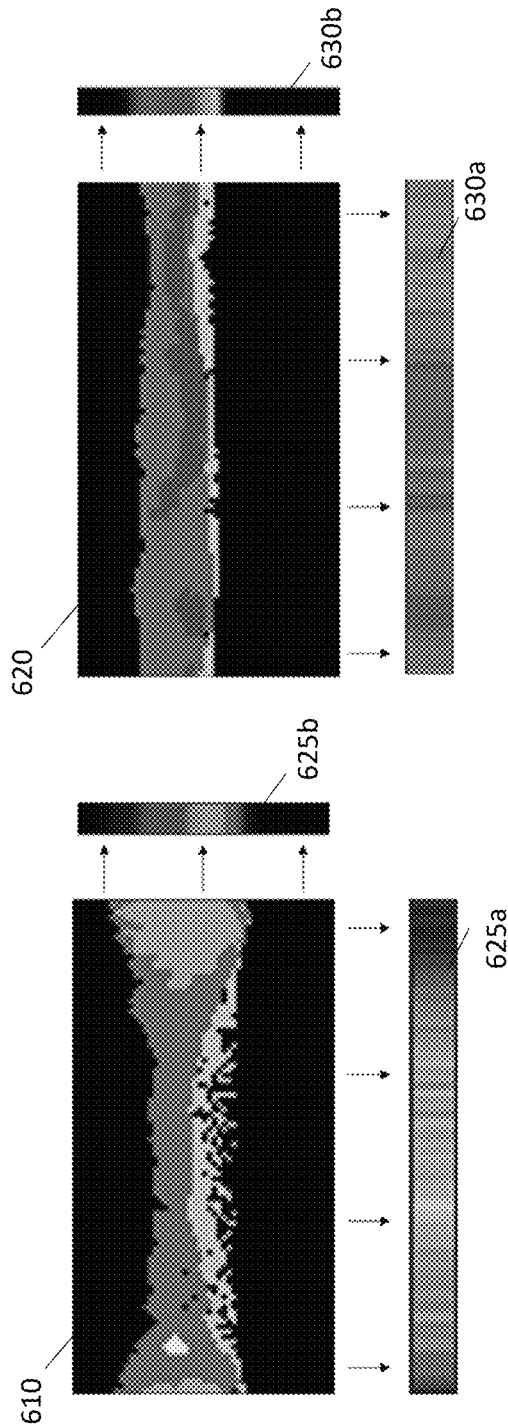
Figure 6B
Figure 6A

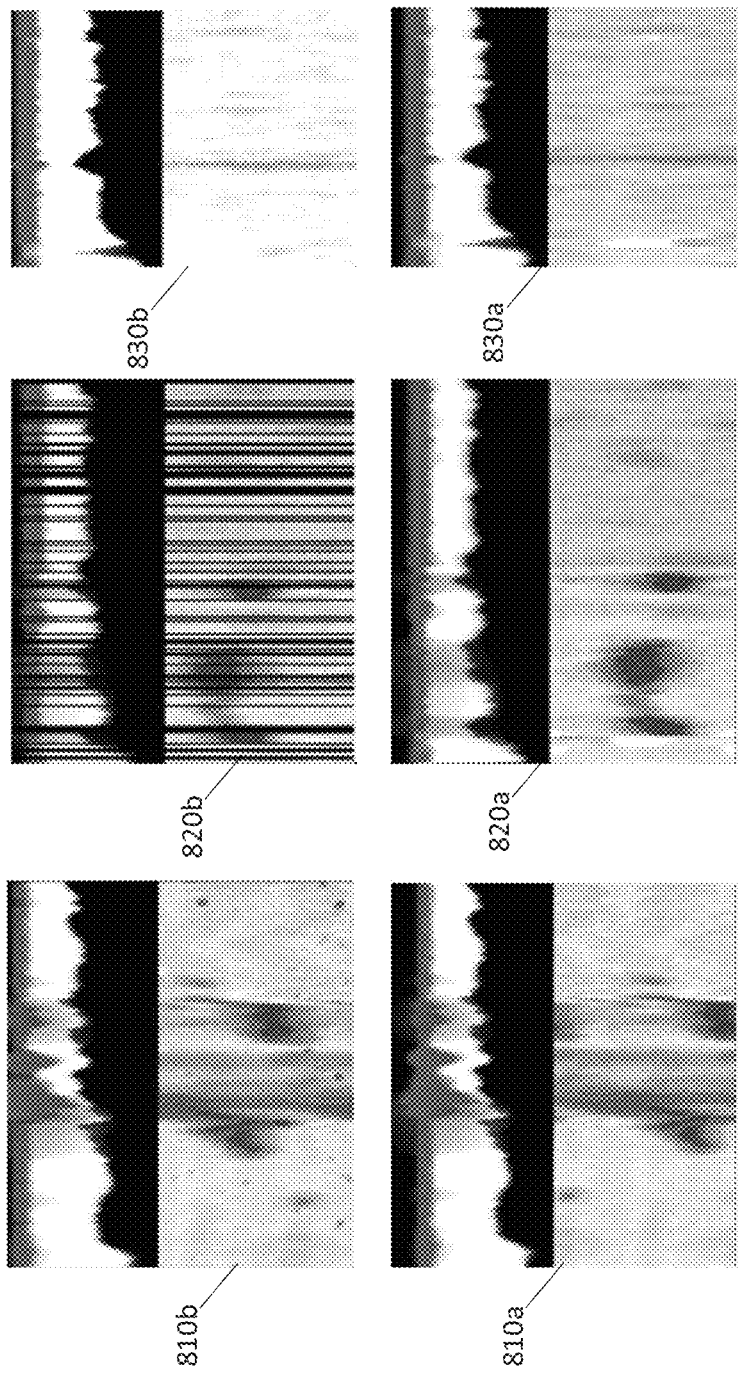

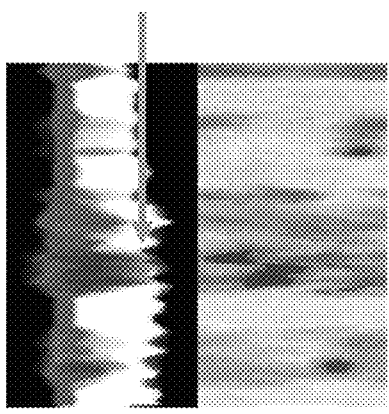
Figure 17A
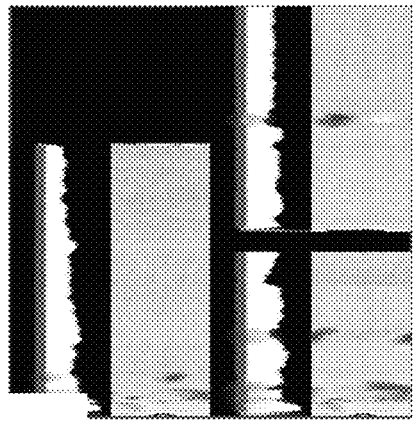
Figure 17B
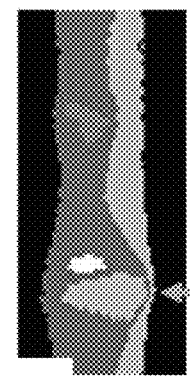
Figure 17C
Figure 17D
1710

STRUCTURED REPRESENTATIONS FOR INTERPRETABLE MACHINE LEARNING APPLICATIONS IN MEDICAL IMAGING

CROSS REFERENCE TO RELATED APPLICATIONS

This application claims the benefit of and priority to U.S. provisional patent application No. 63/424,098, filed on Nov. 9, 2022, the entire contents of which are incorporated herein by reference in its entirety and owned by the assignee of the instant application.

BACKGROUND OF THE INVENTION

Machine learning (ML) models have been used in biomedical image understanding for many years, but the successes of these methods, and its increasing technical readiness to play a role in healthcare, have brought with it significant concerns.

One difficulty can be the degree to which it is possible to answer why the model make the predictions that it makes, which is typically not very high and/or whether performance on training or even test cohorts can extrapolate to the full intended use population. These factors can become more critical as model complexity increases. For example, deep learning neural networks (DNNs) are increasingly considered for use in critical applications because they can perform well but can consequently become harder to explain or interpret (e.g., compared to simpler models) based on, for example, the large degrees of freedom that they incorporate. An ability to explain and/or interpret models can cause a lack of confidence in model results. Therefore, it can be desirable to provide reliable and repeatable creation of interpretable models.

Another difficulty in applying ML to the biomedical space can be sparsity of data. Whereas the development of models in some applications can access millions of images or more, e.g., "scraped" from the internet at very low cost per data point, labeled data in the biomedical domain can be far less available. Labeled data can allow for more reliable ML outcomes. Therefore, it can be desirable to create a labeling process that can incorporate rationale from the experimental sciences rather than being ad hoc.

If these difficulties are overcome together or in combination, patients benefit because the models used in their care or in clinical research are more soundly based.

SUMMARY OF THE INVENTION

Advantages of the invention can include an ability to train an ML model with particularity, an ability to understand why an ML model made the prediction it made, and/or an ability to trust the ML model has been trained to predict what is desired according to principles of formal model interpretability. Another advantage of the invention can include an ability to generate labels accounting for principles of model interpretability. Another advantage of the invention is to enable efficient and robust training on high dimensional inputs, since typical embodiments of the invention invoke biological domain knowledge to dramatically reduce the computational size of model inputs.

In one aspect, the invention can involve a method for creating an interpretable model from patient images. The method can involve receiving, via a processor, imaging data of a region of interest of a patient. The method can also involve processing, via the processor, the imaging data to provide spatially-localized or temporally-localized information. The method can also involve creating, via the processor, a structured representation of the spatially-localized or temporally-localized information that causes at least some of the spatially-localized or temporally-localized information to be indicated as significant spatially-localized or temporally-localized information. The method can also involve using, via the processor, the structured representations for the purpose of training to create the interpretable model, wherein the significant spatially-localized or temporally-localized information contributes to the model inference.

In some embodiments, the method involves using the trained interpretable model for inference. In some embodiments, the method involves creating the structured representation further comprises identifying the significant spatially-localized or temporally-localized information to be indicated as significant based on determining biological features in the spatially-localized or temporally-localized information that impact a desired inference for the interpretable model.

In some embodiments, the spatially-localized or temporally-localized information includes anatomic information, functional information, tissue characteristics, or any combination thereof.

In some embodiments, the interpretable model output is a quantitative imaging response variable. In some embodiments the interpretable model output is a measure of cardiovascular disease status. In some embodiments, the interpretable model output is a hemodynamic property comprising measure of fractional flow reserve, myocardial blood flow, or any combination thereof.

In some embodiments, the interpretable model output is an event prediction. In some embodiments, the event prediction is an adverse cardiovascular event or an adverse neurovascular event. In some embodiments, the interpretable model output is a measure of molecular activity. In some embodiments, the molecular activity pertains to gene expression or protein levels.

In some embodiments, the significant spatially-localized or temporally-localized information is a tubular structure where proximal function of the tubular structure depends at least in part on distal function of the tubular structure.

In some embodiments, the significant spatially-localized or temporally-localized information couples at least two or more structures in the spatially-localized or temporally-localized information where the interpretable model output is dominated by a subset of those structures.

In some embodiments, the significant spatially-localized or temporally-localized information is contiguous tissues that manifest differing molecular activity based on biological processes.

In another aspect, the invention involves a method for creating an interpretable model from patient images. The method can involve receiving, via a processor, imaging data of a region of interest of a patient. The method can involve generating, via the processor, interpretable labels for unlabeled data based on a function that incorporates mechanistic rationale. The method can involve using, via the processor, the interpretable labels for the purpose of training to create the interpretable model, wherein the mechanistic rationale contributes to the model inference.

In some embodiments, the interpretable model output is a quantitative imaging response variable. In some embodiments, the interpretable model output is a measure of cardiovascular disease status. In some embodiments, the interpretable model output is a hemodynamic property comprising measure of fractional flow reserve, myocardial blood flow, or any combination thereof. In some embodiments, the interpretable model output is an event prediction. In some embodiments, the event prediction is an adverse cardiovascular event or an adverse neurovascular event. In some embodiments, the interpretable model output is a measure of molecular activity. In some embodiments, the molecular activity pertains to gene expression or protein levels.

In another aspect, the invention includes a system comprising a processor and a non-transient storage medium including executable instructions configured to cause the processor to receive imaging data of a region of interest of a patient. The executable instructions can be further configured to cause the processor to process the imaging data to provide spatially-localized or temporally-localized information. The executable instructions can be further configured to cause the processor to create a structured representation of the spatially-localized or temporally-localized information that causes at least some of the spatially-localized or temporally-localized information to be indicated as significant spatially-localized or temporally-localized information. The executable instructions can be further configured to cause the processor to use the structured representations for the purpose of training to create an interpretable model, wherein the significant spatially-localized or temporally-localized information contributes to the model inference.

In some embodiments, the executable instructions can be further configured to cause the processor to use the trained interpretable model for inference.

In some embodiments, the executable instructions are configured to further cause the processor to identify the significant spatially-localized or temporally-localized information to be indicated as significant based on determining biological features in the spatially-localized or temporally-localized information that impact a desired inference for the interpretable model.

In some embodiments, the spatially-localized or temporally-localized information includes anatomic information, functional information, tissue characteristics, or any combination thereof.

In some embodiments, the interpretable model output is a quantitative imaging response variable.

In another aspect, the invention involves a system comprising a processor and a non-transient storage medium including processor executable instructions configured to cause the processor to receive imaging data of a region of interest of a patient. The executable instructions can be further configured to cause the processor generate interpretable labels for unlabeled data based on a function that incorporates mechanistic rationale. The executable instructions can be further configured to cause the processor and use the interpretable labels for the purpose of training to create the interpretable model, wherein the mechanistic rationale contributes to the model inference.

In some embodiments, the interpretable model output is a quantitative imaging response variable. In some embodiments, the interpretable model output is a measure of cardiovascular disease status.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, can be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

FIG. 5A shows an example of a cross-section taken from one location of the spatially-localized information of a vessel, according to some embodiments of the invention.

FIG. 5B shows an example of unwrapped cross sections of multiple locations of a spatially-localized information of a vessel, according to some embodiments of the invention.

FIG. 5C shows an example of a single unwrapped cross section remapped into two one dimensional vectors, according to some embodiments of the invention.

FIG. 5D shows the two one dimensional vectors of FIG. 5C stacked into one vector, according to some embodiments of the invention.

FIG. 5E shows an example of a plurality of stacked vectors from unwrapped cross sections concatenated into a structure representation in the final image, according to some embodiments of the invention.

FIG. 6A and FIG. 6B are further examples of unwrapped cross sections of a vessel compressed into two one dimensional vectors, according to some embodiments of the invention.

FIG. 8A, FIG. 8B and FIG. 8C show structured representations, and structured representations after data augmentation, according to some embodiments of the invention.

FIGS. 17A-17F provides examples of structured representations, according to some embodiments of the invention.

It will be appreciated that for simplicity and clarity of illustration, elements shown in the figures have not necessarily been drawn accurately or to scale. For example, the dimensions of some of the elements can be exaggerated relative to other elements for clarity, or several physical components can be included in one functional block or element.

DETAILED DESCRIPTION

One aspect of the present invention can be transforming input data (e.g., CT imaging data) into structured representations, by itself or in combination with adopting a network architectural design that factors in physiological insights before training rather than under-constraining the model or seeking to explain what it learned after training. Another aspect of the current invention can be generating labels synthetically to apply to real data according to a biologically-based labelling technique to guide the model training with a priori mechanistic knowledge. In this way, training may be conducted in two parts, the first dominated by the mechanistic knowledge, and the second to fine-tune model weighing to model output scale without moving away from the mechanistic first step.

Figure 1:
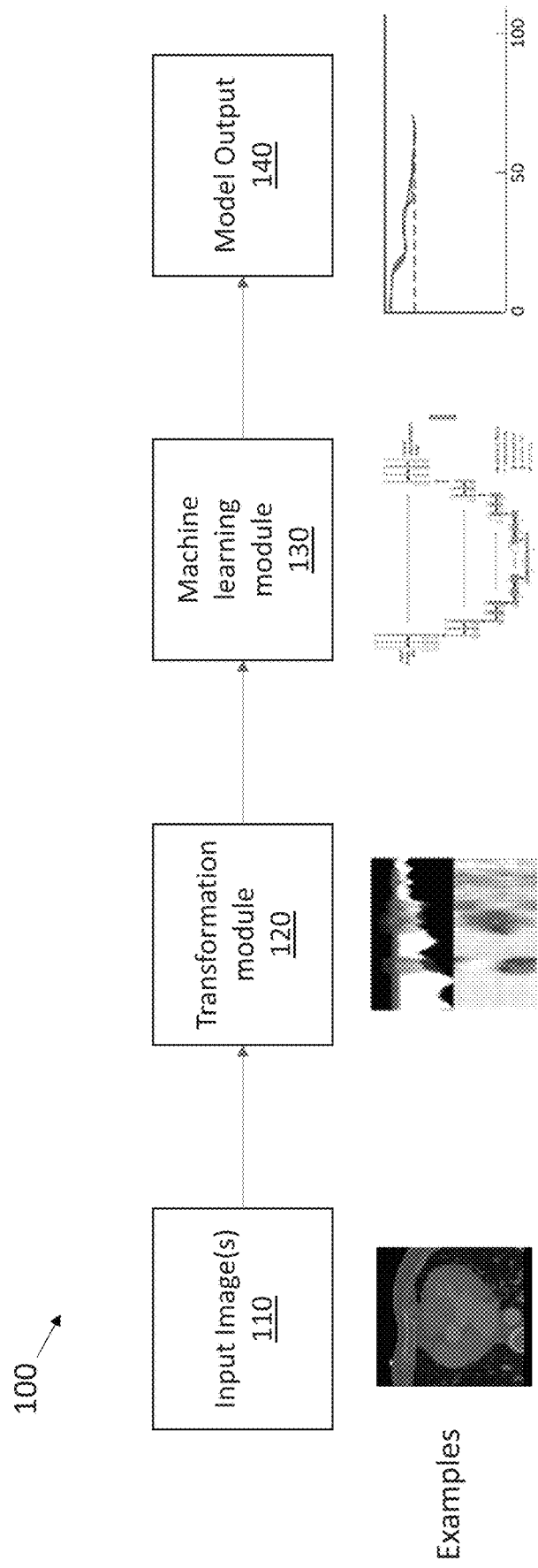
FIG. 1 is a diagram of a system architecture for creating an interpretable model, according to some embodiments of the invention.

FIG. 1 is a diagram of a system architecture 100 for creating an interpretable model, according to some embodiments of the invention. The system architecture 100 includes one or more input image(s) 100, transformation module 120, ML module 130, and output 140. The one or more input image(s) 100 can be input to a transformation module 120. The transformation module 120 can receive the one or more input image(s). The transformation module 120 can transform each of the one or more input images(s) into a corresponding structured representation, where each structured representation includes information that indicates at least a portion of the input that is significant. The transformation module 120 can output one or more structured representations to the ML module 130.

The ML module 130 can be trained to produce the output 140 based on one or more structured representations and/or make predictions once trained with the one or more structured representations as input. Training the ML module based on the one or more structured representations can cause the ML module 130 to be an interpretable model. The ML module can be, for example, a U-Net based CNN. In some embodiments, a number of encoder and decoder layers in the U-Net are increased from 5 to 6. In some embodiments, positional encodings are created—linear gradients—to provide CNN with information about the location of sections within the vessel, and can be concatenated these to the skip layers.

In some embodiments, the model output 140 is a quantitative imaging response variable such as a measure of cardiovascular disease status, for example a hemodynamic property (e.g., fractional flow reserve (FFR), myocardial blood flow, other hemodynamic property, or any combination thereof), or an event prediction. The event prediction can be an adverse cardiovascular event or an adverse neurovascular event, for example heart attack or stroke. In some embodiments, the interpretable model output is a measure of molecular activity. The molecular activity can pertain, for example, to gene expression, protein levels, or metabolites.

Figure 2:
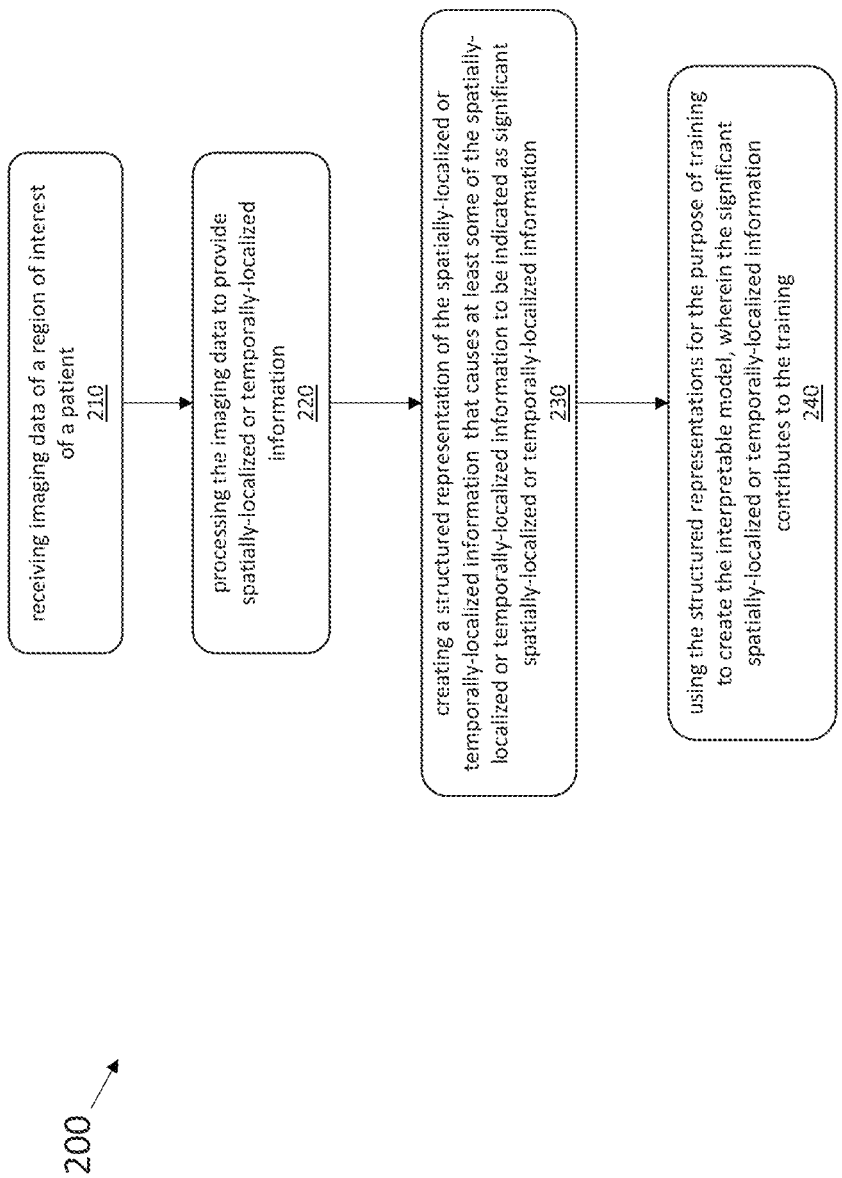
FIG. 2 is a flow chart of a method for creating an interpretable model from patient images, according to some embodiments of the invention.

The method can also involve using the trained interpretable model for inference. FIG. 2 is a flow chart 200 of a method for creating an interpretable model from patient images, according to some embodiments of the invention. For example, as described in step 240, once the interpretable model is trained. In some embodiments, the results of the interference using the interpretable model (e.g., the model as trained as described above in FIG. 2) can be transmitted to a display as a three-dimensional representation, as a graph and/or as a numerical representation. The method can involve receiving imaging data of a region of interest of a patient (step 210). The imaging data can be images of a patient. The imaging data can be a region of interest (e.g., a part of a patient that is of interest). The imaging data can be taken with any medical imaging modality, for example computed tomography (CT), dual energy computed tomography (DECT), spectral computed tomography (spectral CT), photon counting CT (pCT), computed tomography angiography (CTA), cardiac computed tomography angiography (CCTA), magnetic resonance imaging (MRI), multi-contrast magnetic resonance imaging (multi-contrast MRI), nuclear medicine (e.g., PET or SPECT), optical coherence tomography (OCT), near-infrared spectroscopy (NIRS), and/or ultrasound (US).

Figure 3:
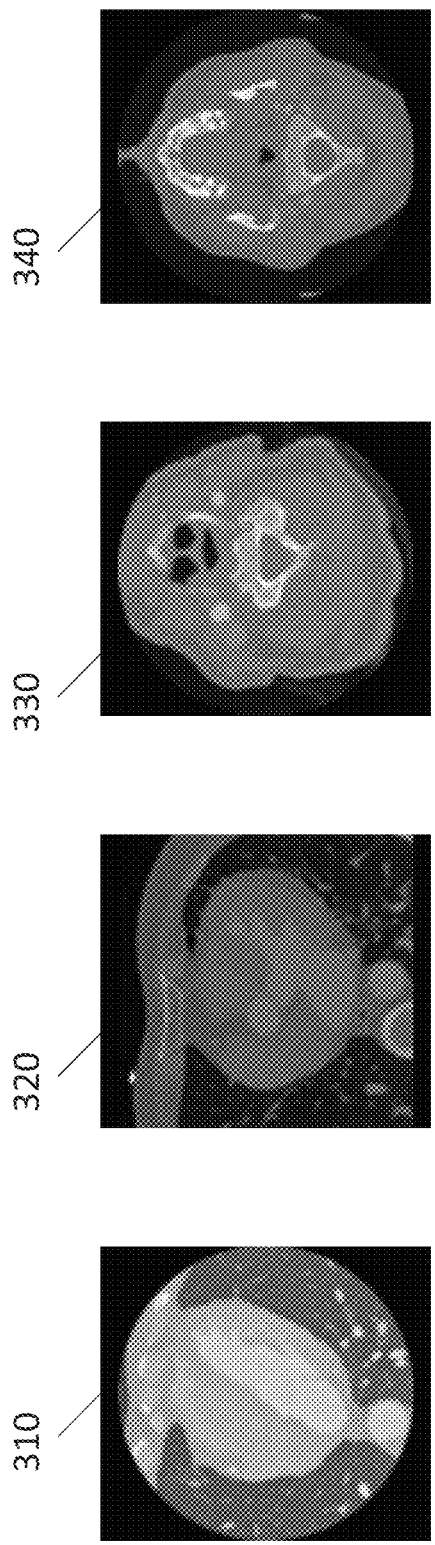
FIG. 3 shows examples of input images of coronary and carotid vessels, according to some embodiments of the invention.

Turning to FIG. 3, FIG. 3 shows examples of input images (e.g., raw input images) of coronary and carotid vessels, according to some embodiments of the invention. The input images 310, 320, 330, and 340 of FIG. 3 are CT scans. Although the example in FIG. 3 shows vessel input, other anatomical structures can be used. For example, airway tubes, lungs, tumors, and/or any anatomical structure that can be imaged.

The method can involve processing the imaging data to provide spatially-localized and/or temporally-localized information (step 220). The spatially-localized information can be information in the imaging data that is indicated relative to spatial distributions in the input image. In some embodiments, spatially-localized information can include anatomic information (e.g., what is near or far from other structures), tissue characteristics (e.g., hemorrhage, calcification, lipids, necrotic tissue, etc.) functional information (e.g., level of metabolic, oxygenation, perfusion, distensibility, etc.), or any combination thereof.

The temporally-localized information can be information in the imaging data that is indicated relative to the imaging data taken at particular times. The temporally-localized information can be, for example, how quantities or qualities change over time spans, both short- and long time spans, what comes first vs. later, whether a quantity or quality is increasing or decreasing, the rate of change, or higher orders of change such as acceleration, progression, regression, etc.

Figure 4C:
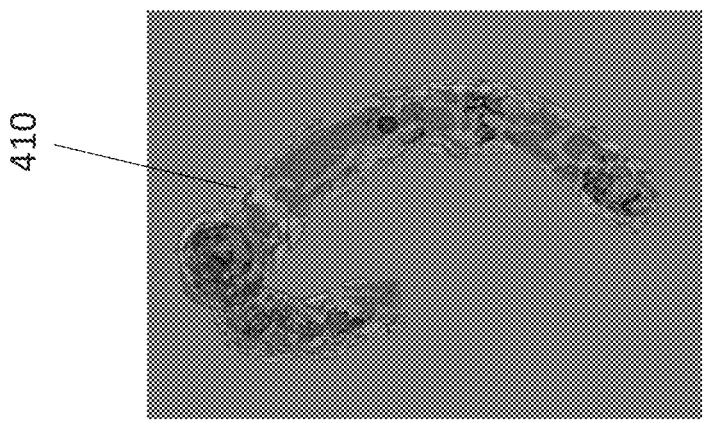
FIGS. 4A, 4B, and 4C show a three-dimensional view of a vessel with the spatially-localized information highlighted as shown in patterns.
Figure 4B:
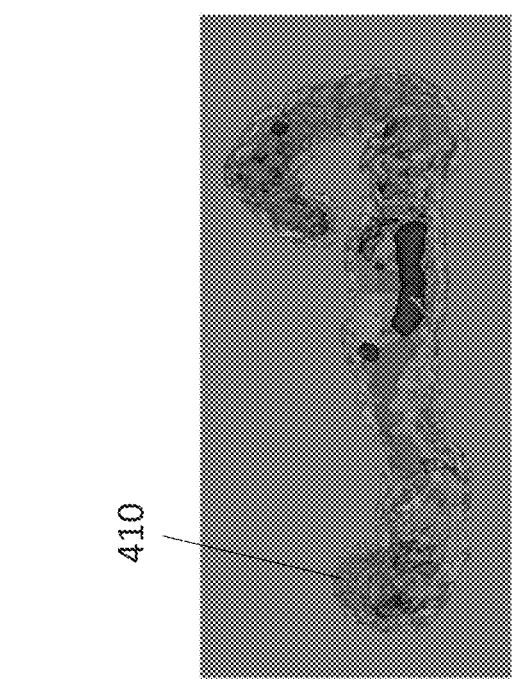
Figure 4A:
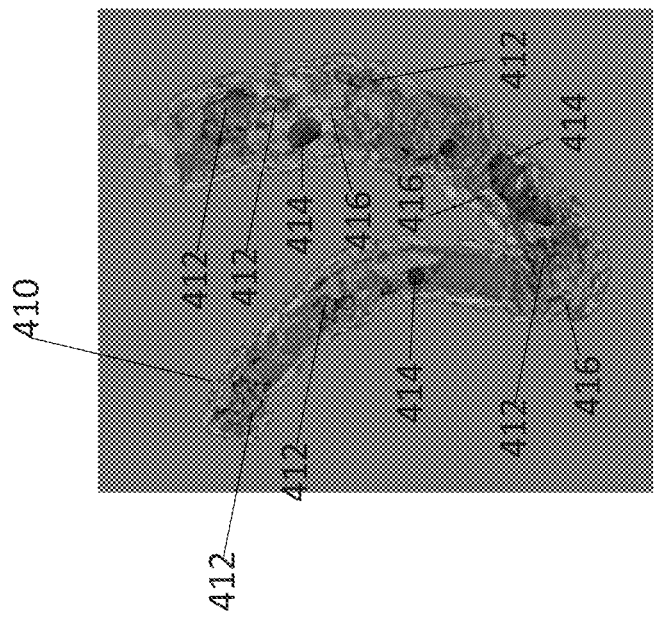

Using the vasculature example as illustration, turning to FIGS. 4A, 4B, and 4C, FIGS. 4A, 4B, and 4C are examples drawn from segmented subsets of input image of FIG. 3 processed to provide spatially-localized information. FIGS. 4A, 4B, and 4C show a three-dimensional view of a vessel 410 with the spatially-localized information highlighted as shown in patterns. The first spatially-localized information 412 indicates blood, the second spatially-localized information 414 indicates lipids, and the third spatially-localized information 416 indicates calcification in the vessel walls of the vessel.

Turning back to FIG. 2, the method can involve creating a structured representation of the spatially-localized or temporally-localized information that causes at least some of the spatially-localized or temporally-localized information to be indicated as significant spatially-localized or temporally-localized information (step 230). The spatially-localized or temporally-localized information that is indicated as significant emphasizes the information with a mechanistic rationale tying the significant information to the interpretable model output while diminishing the information that has not been indicated as being significant.

In some embodiments, identifying the significant spatially-localized or temporally-localized information to be indicated as significant based on determining biological features in the spatially-localized or temporally-localized information that impact a desired inference for the interpretable model.

For a detailed example, described here, the target task is the estimate of Fraction Flow Reserve (FFR) of the coronary vasculature[11, 12]. FIG. 5 shows an example of a vessel processed to accentuate biologically significant tissue behavior and relative rather than absolute relationships proximal to distal, having spatially-localized information 510-515 (e.g., vessel as shown above in FIG. 4A). FIG. 5A shows an example of a cross-section 610 taken from one location of the spatially-localized information of a vessel, according to some embodiments of the invention, processed into a sequence (FIG. 5B) of unwrapped cross-sections (516), according to some embodiments of the invention.

In FIG. 5B, each rectangle 510a, 510b . . . 510n, represents one cross section along a centerline at 0.5 mm of its respective vessel (not shown) at 0.5 mm spacings with spatial relationships expressed in an idealized rather than in original coordinate system to emphasize relationships which matter mechanistically while simultaneously reducing nuisance variation for spurious information. From left to right indicates proximal to distal ends of the vessel. FIG. 5A shows information of tissue type of a lumen 514a, 514b, . . . 514n, generally 514, lipid-rich necrotic core (LRNC) 515, lumen 513, focal regions of CALC 519, . . . generally, 522 and wall 511.

Continuing, FIGS. 5C through 5E show an example of creating a structured representation of the spatially-localized information of a vessel (e.g., vessel as shown above in FIG. 4), according to some embodiments of the invention.

The cross-section locations are taken at a region of interest defined by the relationship to model output. In some embodiments, hundreds of cross sections can be taken, or other shapes that are associated with the biological mechanism of the model output.

FIG. 5C shows an example of a single unwrapped cross section e.g., section 510c of FIG. 5B, remapped into two one dimensional vectors, 525a and 525b, respectively. In one example embodiment, the tissue type proportions are averaged across the horizontal, and then vertically. In this embodiment, horizontal averaging includes the background as a tissue type but vertical averaging does not. These proportions can be converted to RGB values, resulting in a 1D RGB array corresponding to horizontal averaging and another 1D RGB array corresponding to vertical averaging. Each one-dimensional vector can be converted to RGB values, resulting in one dimensional RGB arrays.

The resultant one-dimensional vector 525a shows mapping between the wall 511, lumen 513, LRNC 515, CALC 517, and IPH 519 and vector 525a, and vector 525b.

FIG. 5D shows the two one dimensional vectors, 525a and 525b stacked into one vector, 530.

In this manner, a complex 3D volume can be represented as a relatively small 2D RGB image, emphasizing the biologically relevant information while de-emphasizing nuisance variation.

As is apparent to one of ordinary skill in the art, all of the unwrapped cross sections can be remapped as described in FIG. 5C and stacked as described in FIG. 5D, to create a plurality of stacked vectors, one for each unwrapped cross section.

FIG. 5E shows an example of a plurality of stacked vectors (e.g., from unwrapped cross sections, determined as described with respect to FIGS. 5C and 5B above), concatenated into a final image which in this example, of the vessel input, the structure representation in the final image. The concatenation can place each stacked vector next to another stacked vector in the same order as the unwrapped cross section (e.g., in the order that the cross-section data is present in the vessel). FIG. 6A and FIG. 6B are further examples of unwrapped cross sections 610 and 620 of a vessel compressed into two one dimensional vectors (e.g., as described above with respect to FIGS. 5A-5C), 625a and 625b, 630a and 630b, respectively, according to some embodiments of the invention. FIG. 6A shows high spatial-frequency information, for example, fragmented appearance of the lumen is preserved, and FIG. 6B shows that IPH lesions are localized within the two one dimensional vectors.

In some embodiments, the final image can be 34 KB on disk and have dimensions 200×181. This can be a 1000× reduction in size from the categorical 3D image shown in FIG. 4A and a 200× reduction in size from an original CT image volume.

The spatially-localized information and/or structured representations can save computing space and/or reduce computing complexity and/or time. For example, for the vessel example shown in FIG. 5A-5E, for a storage disc of 35 MB and a size of an original input image (e.g., CT scan subvolume) of 7 MB, the spatial dimensions of the computing stored volume can be 94×105×179D. Post-reduction, the size of the final image can be approximately 34 KB and have dimensions 200×179.

Figure 7C:
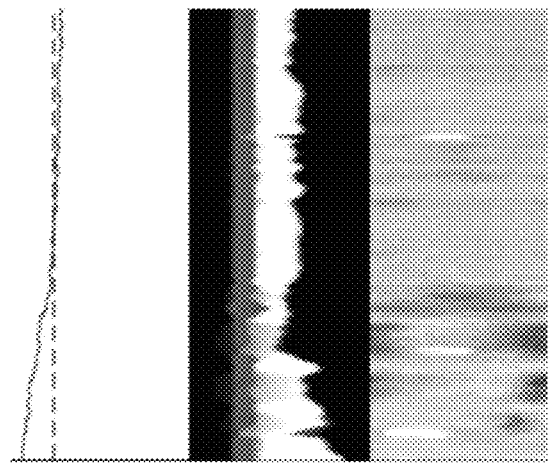
FIG. 7A, FIG. 7B and FIG. 7C are examples of structured representations of vessels shown with densely labeled FFR, according to some embodiments of the invention.
Figure 7B:
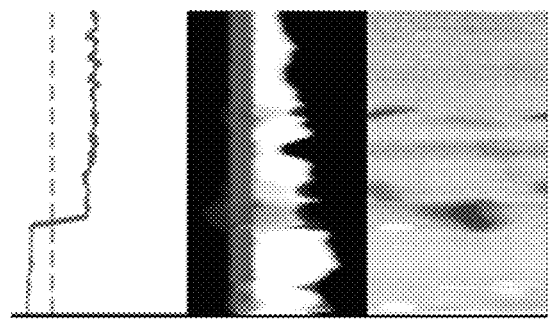
Figure 7A:
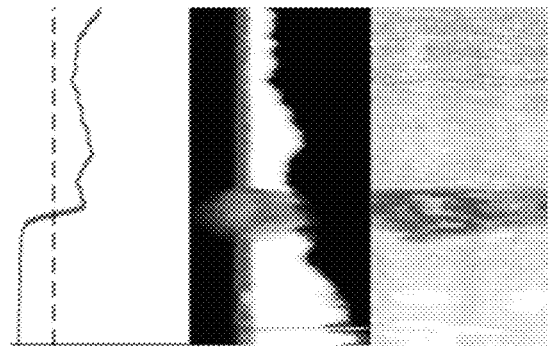

Staying with the FFR example, FIG. 7A, FIG. 7B and FIG. 7C are examples of structured representations (e.g., as shown above in FIG. 5E), of vessels shown with densely labeled FFR (e.g., as shown above in each corresponding plot of FFR values from proximal to distal ends of the vessel), according to some embodiments of the invention. In each of FIG. 7A, FIG. 7B and FIG. 7C, ground truth is represented as FFR value from proximal to distal end of the vessel, blue trace being (black dashed line representing 0.8). In FIG. 7A, a focal LRNC, localized remodeling, and strong vessel taper can be seen (the fact that white area decreases sharply moving distally). In FIG. 8A, moderate CALC with an irregular luminal surface in the vessel can be seen. In FIG. 8C, lower levels of CALC and IPH, tapers quickly proximally, and exhibits less tapering distally in the vessel can be seen.

FIG. 8A, FIG. 8B and FIG. 8C show structured representations 810a, 820a, and 830a, and structured representations after data augmentation 810*b*, 820*b*, and 830*b*, according to some embodiments of the invention. Image 810*b* shows pathological patch noise, image 820*b* shows section dropout and image 830*b* shows contrast augmentation.

Figure 9C:
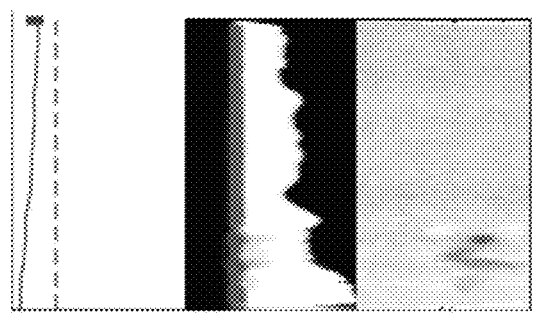
FIG. 9A, FIG. 9B and FIG. 9C are examples of vessels with minimal disease, according to some embodiments of the invention.
Figure 9B:
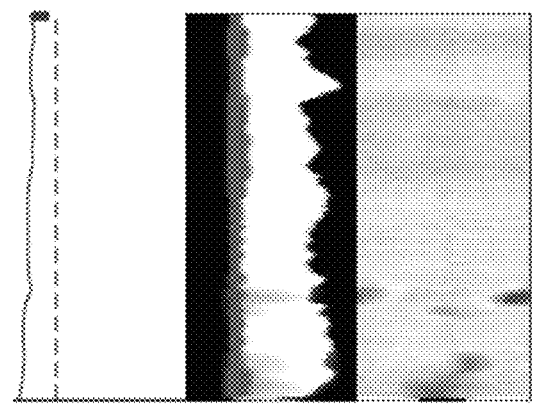
Figure 9A:
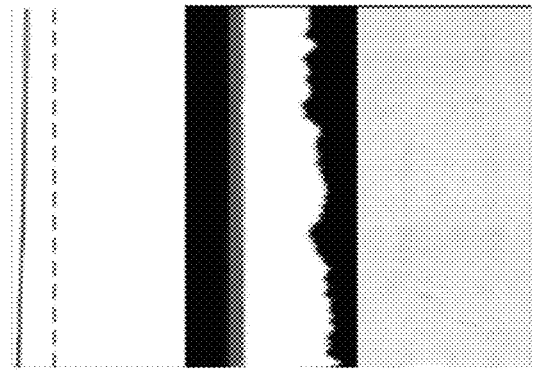
Figure 10A:
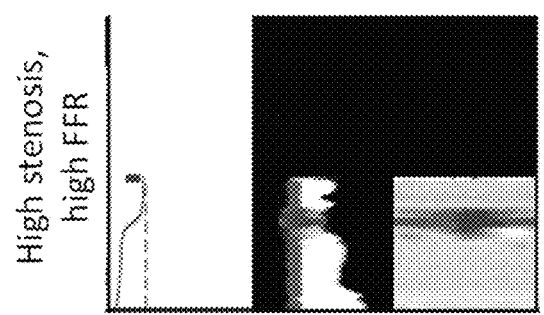
FIG. 10A, FIG. 10B, FIG. 10C and FIG. 10D are examples of vessels demonstrating focal drops in various combinations of FFR and stenosis, with the top portion of the graph being predictions, and the bottom portion showing the corresponding structured representation using the interpretable model and the process described in FIG. 5A through 5E as described above, according to some embodiments of the invention.
Figure 10B:
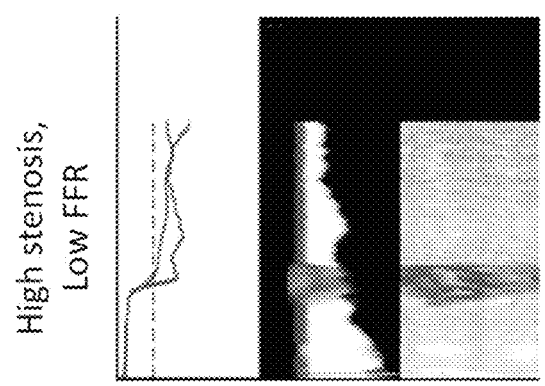
Figure 10C:
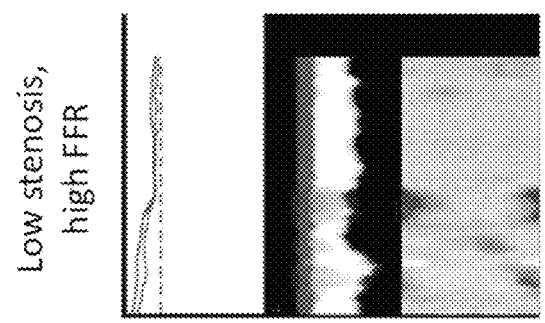
Figure 10D:
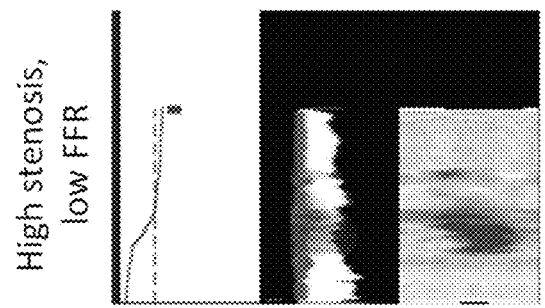

FIG. 9A, FIG. 9B and FIG. 9C are examples of vessels with minimal disease, according to some embodiments of the invention. The graph lines above the dashed lines show predicted FFR and the graphs below the dashed lines show the corresponding structured representation using the interpretable model and the process described in FIG. 5A through 5E as described above.

FIG. 10A, FIG. 10B, FIG. 10C and FIG. 10D are examples of vessels demonstrating focal drops in various combinations of FFR and stenosis, with the top portion of the graph being predictions, and the bottom portion showing the corresponding structured representation using the interpretable model and the process described in FIG. 5A through 5E as described above, according to some embodiments of the invention.

Figure 11C:
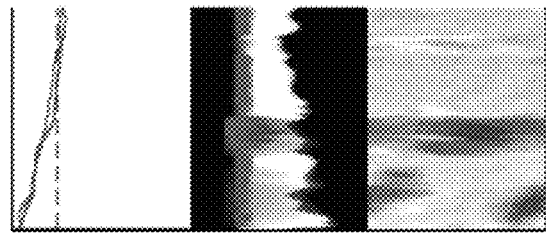
FIG. 11A, FIG. 11B and FIG. 11C are examples of vessels with diffuse disease, according to some embodiments of the invention.
Figure 11B:
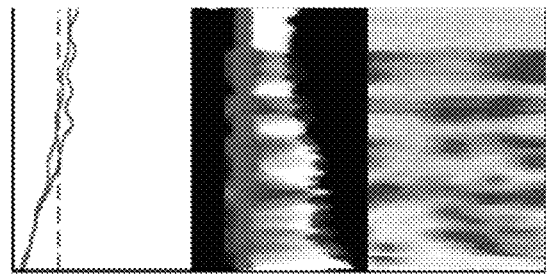
Figure 11A:
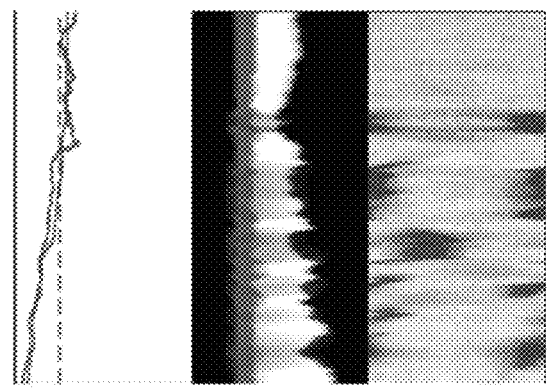

FIG. 11A, FIG. 11B and FIG. 11C are examples of vessels with diffuse disease, according to some embodiments to the invention. The top portion of the graph being predicted FFR and the graphs below the dashed lines show the corresponding structured representation using the interpretable model and the process described in FIG. 6A through 6E as described above.

Turning back to FIG. 2, the method can involve using the structured representations for the purpose of training to create the interpretable model, wherein the significant spatially-localized or temporally-localized information contributes to the training (step 240).

In some embodiments, another aspect may be used in combination with, or separately from, the structured representations. Specifically, labeling of unlabeled training data may proceed from evaluation of a mechanistically-motivated synthetic labeling scheme based on biological bench science. By way of example, the interpretability of a model can be improved for example by being trained in two phases, with application from another inventive aspect regarding labelling.

First, the thousands of unlabeled vessels can be exploited. Synthetic "pseudo-FFR" labels are created for the vessels using the technique described here by way of example. Synthetic labels, e.g., synthetic FFR, was generated in three steps. Morphological analysis produces per-section measurements of lumen area, calcification, etc.; we used this to calculate the instantaneous (per-section) disease burden, IDB.

$$IDB(x)=1/(1+\exp(\alpha-x)-1/(1+\exp(\alpha))$$

where x is the sum of CALC, LRNC, and IPH area (mm2), plus a value corresponding to the narrowing of the lumen (stenosis). This stenosis value was linearly corrected to discount natural tapering. The value of a was set to 4.5. The second step was to integrate this signal and convert it from monotonically increasing to monotonically decreasing using this equation:

$$psffr=1.0-\text{cumsum}(k*IDB)$$

where 'psffr' abbreviates 'pseudo-FFR' and k is a scaling value set to 0.05. Finally, this signal was rescaled such that the distribution of final FFR values across the population of pseudo-FFR signals approximated the distribution of FFR values in labeled training data. The resulting pseudo-FFR signal has the characteristic monotonicity and range of the real signal, and its decreases are deterministically and directly related to the tissue characteristics of the vessel. By illustration, a model could be trained on these 6768 synthetically labeled vessels. In light of the relatively high N, a 90/10 train-validation split can be used in this stage. The training can begin with a learning rate of 0.001, and the learning rate can be divided by 5 when the validation loss does not decrease for five consecutive epochs. After three such sequences of non-decreasing validation loss, training can be halted. Loss can be calculated based on the mean square error with additional components penalizing endpoint discrepancy and violations of downward monotonicity.

Continuing the example, in the second stage, a model pre-trained as in the first stage can be fine-tuned as used as the labeled data. The training can be similar, except that k-fold validation can be employed and repetition run in the training for k=4 for a train-validation split of 75/25. The learning rate and training schedule are the same as in the first stage. The final model was an ensemble of the 4 trained models, formed by averaging their predictions A hyperparameter search over parameters controlling dataset augmentation was undertaken to create the final model, with three repetitions per hyperparameter combination. Thus, the full k-fold validation, with repetitions, can be performed for each sampled hyperparameter combination. The hyperparameter combination which produced models with the highest minimum on the validation data, as averaged across all repetitions and folds, can be used to generate a new model, which can be the averaged ensemble of the models for that hyperparameter combination (restricted those from the best-performing repetition). This model can be run on the final holdout data to produce the performance measures reported in this application. Occasionally, for very long vessels, the signal generated by the model can rise anomalously at the distal end. To counteract this, we enforced a monotonicity constraint in inference whereby the signal, generated from proximal to distal endpoints, can be clamped to the running minimum plus 15%. The clamped signal can be used in model inference.

Figure 12A:
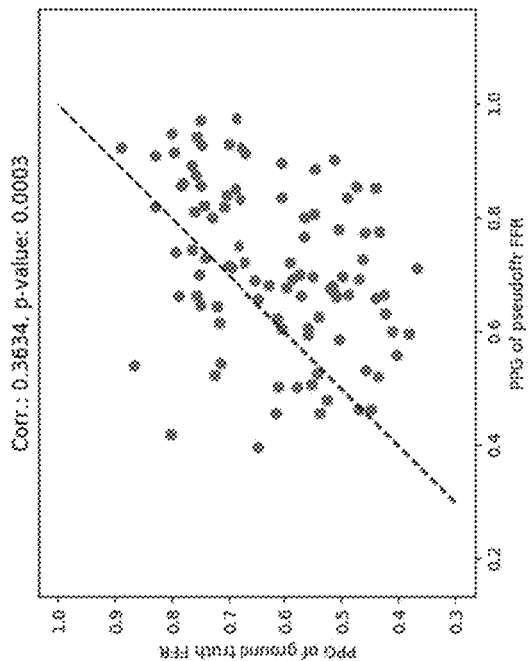
FIG. 12A and FIG. 12B presents graphs of predicted vs. ground truth PPG across densely labeled vessels in FIG. 12A, according to some embodiments of the invention.
Figure 12B:
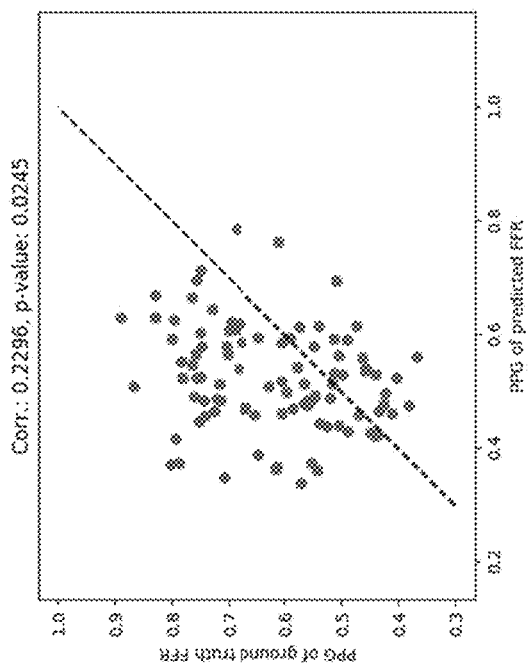
Figure 13A:
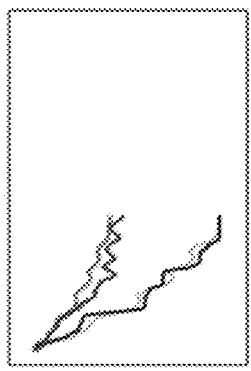
FIGS. 13A through 13F shows examples of predictions from the fine-tuned model, and predictions from a model trained "from scratch", e.g., without prior pre-training but otherwise identical parameters, according to some embodiments of the invention.
Figure 13D:
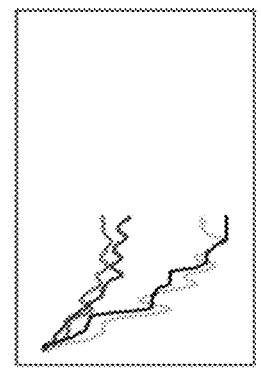
Figure 13B:
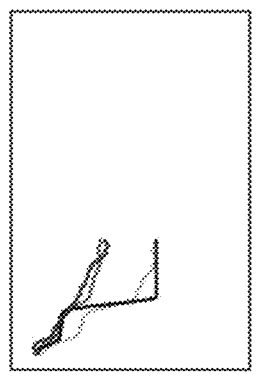
Figure 13E:
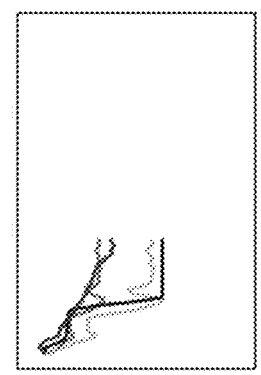
Figure 13C:
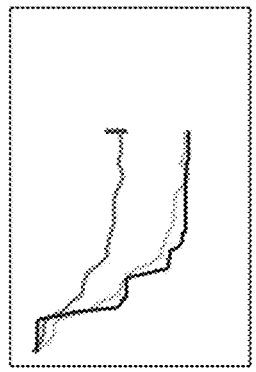
Figure 13F:
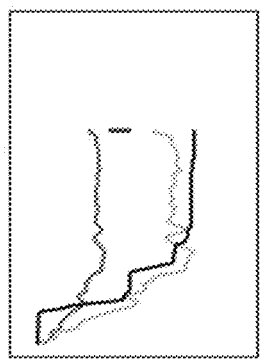

As an illustrative exploration, coronary vascular disease presents on a spectrum from focal to diffuse, as determined by the distribution of disease within the vessel. Correspondingly, FFR drop across the vessel's length can be abrupt, e.g., spatially localized or gradual. The drop in FFR can be quantified by a Pullback Pressure Gradient (PPG) index, ranging from 0 (e.g., gradual) to 1 (e.g., spatially localized). In some embodiments, PPG on an example dataset can result in a distribution (e.g., mean: 0.62, std. dev.: 0.13) similar to that in found in the art (e.g., mean 0.57, std. dev. 0.18). In some embodiments, the PPG for trained model predictions can be such that distribution is shifted and/or narrower (e.g., mean 0.52, std. dev. 0.09). A shifted and/or narrower distribution can be attributed to this to the model 'hedging' its estimate of sharp drops to avoid error (e.g., Type I error). A correlation between the PPG indices can be derived from ground truth and the model prediction. FIG. 12A and FIG. 12B presents graphs of predicted vs. ground truth PPG across densely labeled vessels in FIG. 12A, Pseudo-FFR and FIG. 12B ground truth PPG, according to some embodiments of the invention.

For example, as shown in FIG. 12A, as positive and significant. Ground truth PPG can be compared to PPG derived from the synthetic labels, for example, as shown in FIG. 12B, showing an even stronger correlation. The stronger correlation in the synthetic labels case can be attributed to the fact that in this example, the synthetic labels are constructed almost solely to reflect disease burden, which is what PPG measures, and was largely unconstrained by FFR accuracy.

FIGS. 13A through 13F shows examples of panels a-c) predictions from the fine-tuned model, and d-f) show predictions from a model trained "from scratch", e.g., without prior pre-training but otherwise identical parameters, according to some embodiments of the invention. Model predictions (red) are shown alongside the synthetic labels from the pre-training dataset (black), and have been rescaled to match the minimum value of the synthetic label (yellow). Ground truth is shown for reference (blue). The predictions of the pretrained, fine-tuned model match the contours of the synthetical label well after rescaling. When the model is trained without pre-training the similarity of the predicted signal to the interpretable signal is much weaker.

FIGS. 4-13 show examples of the significant spatially-localized or temporally-localized information that is a tubular structure where proximal function of the tubular structure depends at least in part on distal function of the tubular structure.

Figure 14:
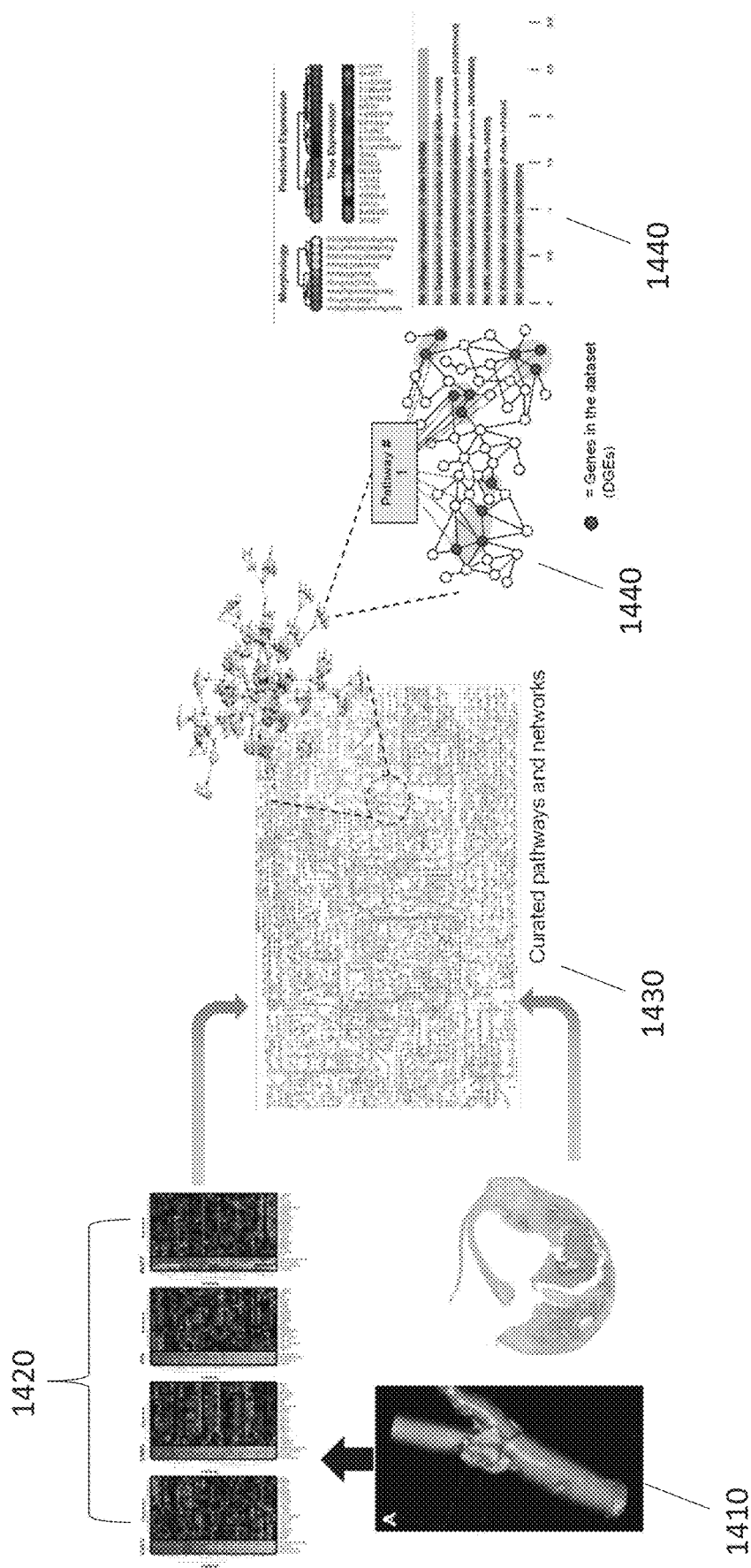
FIG. 14 is a diagram of a flow for developing a model that predicts or estimates molecular activity as an output where the input is a vascular image, according to some embodiments of the invention.

As an additional example embodiment, FIG. 14 is a diagram of a flow for developing a model that predicts or estimates molecular activity as an output where the input is a vascular image, according to some embodiments of the invention. In the FFR example, the model output is a number signifying a hemodynamic characteristic that changes proximally to distally in a vessel, but in the molecular activity example, the model output is the varying molecular activity across disparate distributions of tissues. A shared characteristic of the examples can be a requirement to trust model predictions, but there are differences that advantageously utilize very different structured representations and synthetic labeling schemes. In both cases, interpretability of a model's response benefits from optimizing the information content of the model inputs, but in the molecular activity example, accommodation can also be made for the highly granular set of potential model outputs and the relationships therein.

As shown in FIG. 14, a processed input imaged can be input as spatially-localized information 1410 into one or more interpretable models (e.g., interpretable models as created above in FIG. 2), to output biological activity as the levels of molecular species and/or pathway regulation 1430. The biological processes being determined can be output as a complex network where one or more molecules, pathways, or both can be estimated as one or more model outputs, as shown by 1440.

Figure 15A:
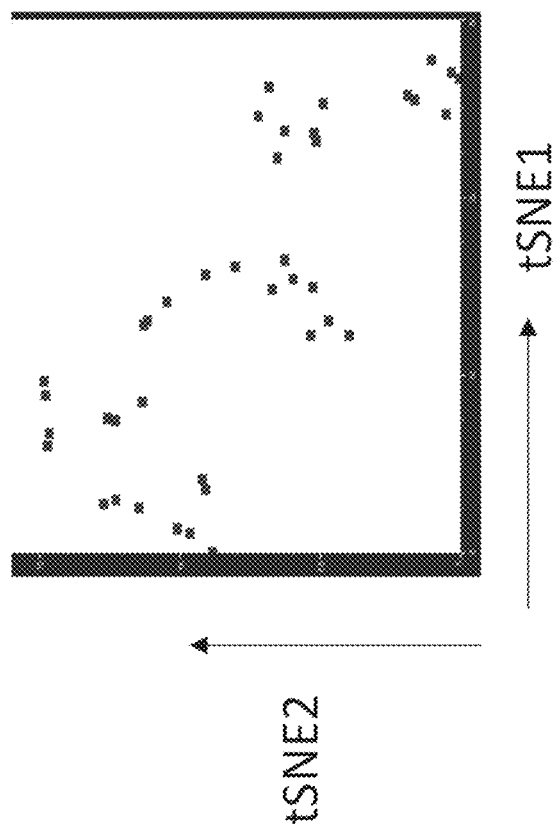
FIG. 15A and FIG. 15B show using principal component analysis (PCA) into five principal components, according to some embodiments of the invention.
Figure 15B:
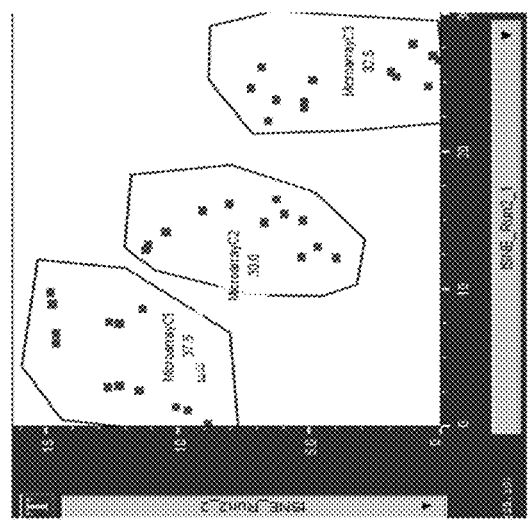

In some embodiments, the method can advantageously account for dimensionality reduction of genes, for example, as can be shown using principal component analysis (PCA) into five principal components (FIGS. 15A and 15B). The gene expression variability may be visualized among samples by using t-distributed stochastic neighbor embedding (tSNE) with the principal components as variables. Samples may be clustered, and the clustering may be cross-validated with histologic phenotype (e.g., CALC or LRNC). Differential gene expression (DEG) may be performed with analysis by dichotomized fold change between clusters (e.g., CALC vs. LRNC). For example, dimensionality reduction of 3,485 genes among 40 samples using PCA into five principal components. Further reduction of dimensionality may be achieved using t-distributed stochastic neighbor embedding (tSNE) by using the principal components as variables for the tSNE, that explains the variability of gene expression among the samples (FIG. 15A). Clustering of the samples and cross-validating the clustering with histologic phenotype (FIG. 15B). DEG analysis by dichotomized fold change between clusters (e.g., CALC vs. LRNC) may be filtered, for example with a false discovery rate (FDR)<0.05, fold change (FC)>1.5. Example results for illustrative purposes only: CALC predominant cluster of specimens have 168 DEGs and LRNC predominant cluster of specimens have 60 DEGs, representing a considerable reduction in complexity to avoid overfitting of models on practical numbers of samples, which incorporate biological and mechanistic rationale that would otherwise lead to requiring much larger numbers of model output variables. The spatially localized information of characterized tissues can thereby be represented effectively by such clusters.

Figure 16:
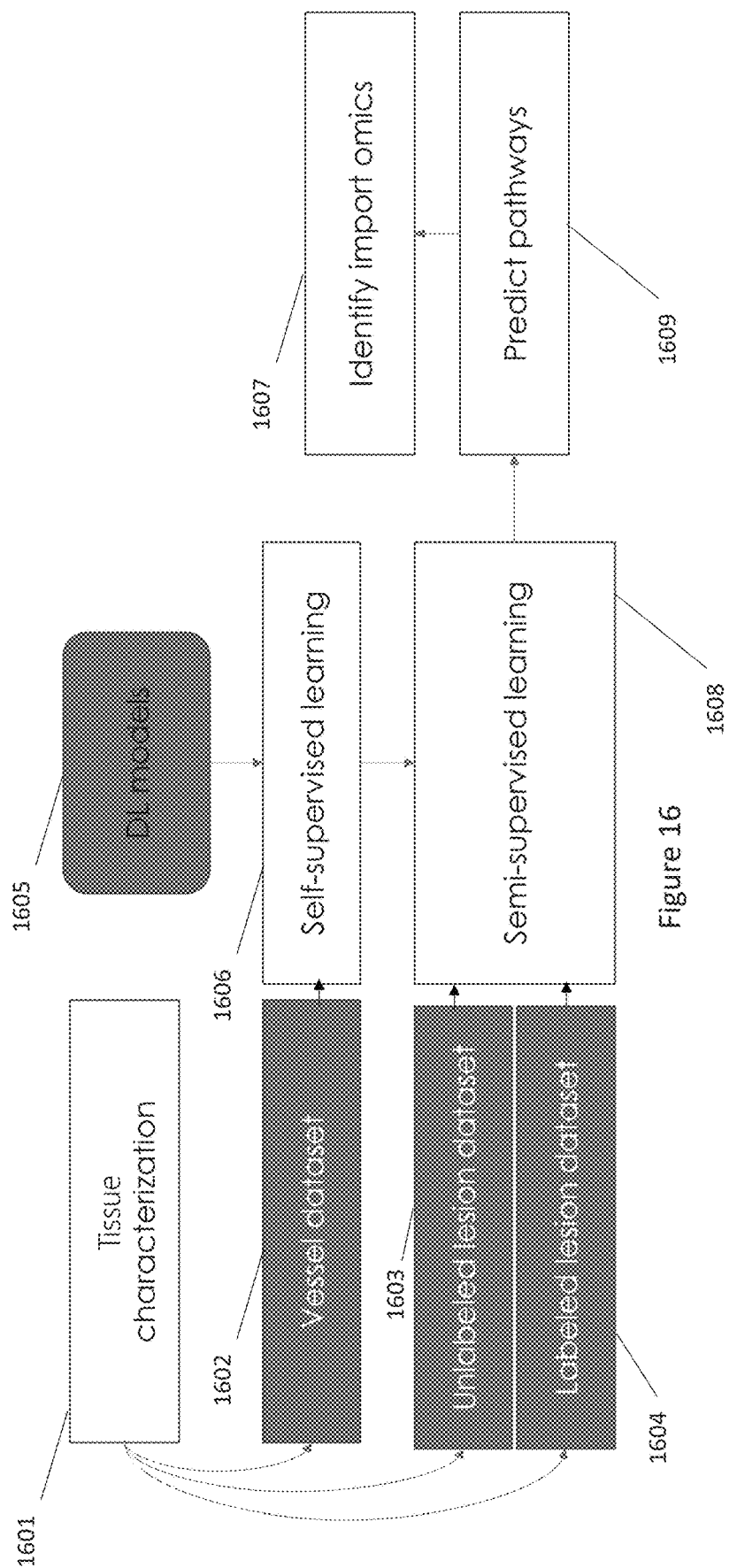
FIG. 16 is a flow chart for a method for creating an interpretable model from patient images, according to some embodiments of the invention.

FIG. 16 is a flow chart for a method for creating an interpretable model from patient images, including reducing overfitting, that may be used in combination with, or separately from, the example of FIG. 15, according to some embodiments of the invention. Tissue characterization data 1601 can be used in a vessel dataset 1602. The tissue characterization 1601 can be input to unlabeled 1603 or labelled 1604 datasets to drive self-supervised learning 1606. Each of these learning methods (unlabeled and labeled) may be used to train DL models 1605. In some embodiments, the unlabeled and/or labeled datasets can be used to train linear regression models, generative adversarial networks (GANs), nearest-neighbor approaches, and/or other models as are known the art. These models can predict or estimate the levels of individual molecules, clusters of molecules, or pathways of molecules, using methods such as practiced in systems biology for example that access pathway diagrams or databases that identify constituent molecules that participate as a group based on interactions 1609. Since there are fewer pathways than molecules, a reduction of model outputs is achieved without losing important biological activity information and incorporating mechanistic information into the model output.

FIGS. 14-16 show an example of the significant spatially-localized or temporally-localized information as contiguous tissues that manifest differing molecular activity based on biological processes.

FIGS. 17A-17E provides further examples of structured representations, according to some embodiments of the invention.

FIG. 17A shows an example of a structured representation of a vessel having spatially-localized information arising from a significance put on uniform weighting of tissue components, according to some embodiments of the invention.

FIG. 17B shows an example of the structured representation of the vessel of FIG. 18A with extra weight added to the pathological tissue components, which may be preferred according to some embodiments of the invention.

FIG. 17C shows an example of a structured representation having a significance placed on an area 1710, such that it can be readily identified by an interpretable algorithm, which may be preferred according to some other embodiments of the invention. FIG. 17D highlights another example embodiments. For major adverse cardiovascular event (MACE) prediction, it is necessary to represent the entire coronary vasculature; a MACE-causing rupture could arise from any vessel. To this end, elements from the single vessel example can be combined from multiple vessels to form a patient-level representation (FIG. 17D). The increased size of the representation can require a larger model and can enable estimation of per-patient response variables which may not be possible with single structured representations alone. This structured representation can also allow representation for missing data (e.g., if a vessel was not in the field of view, the adverse event prediction can be based on the subset that were there, and if vessels cooperated in conferring risk, this can be represented efficiently. Without loss of generality this example can be extrapolated on, for example, in a model tasked with predicting adverse neurovascular events from the cerebrovascular system.

Figure 17F:
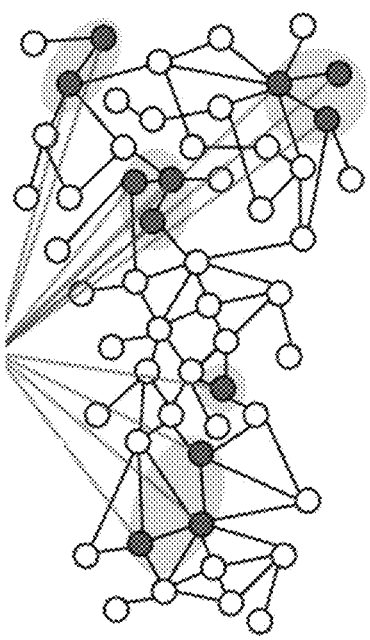
Figure 17E:
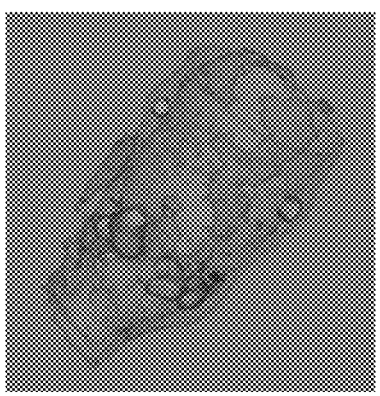

FIG. 17E and 17F that the spatially-localized information maps to a biological network representation for determining molecular activity from patient images to optimize adjacency of tissue over orientation of tissue, and utilize training steps to move from macroscopic tissue distributions down the molecular activity using an intermediary pathway representations to control for overfitting, according to some embodiments of the invention.

FIGS. 17A-17F show examples where the significant spatially-localized or temporally-localized information loosely connected structures where a model output may be dominated by a subset of those structures, and extended applications for molecular activity profiling.

Although embodiments of the invention are not limited in this regard, discussions utilizing terms such as, for example, "processing," "computing," "calculating," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by an apparatus and can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device, a transmitting device, and/or a computing device. The display device can be, for example, a cathode ray tube (CRT) and/or a liquid crystal display (LCD) monitor. The interaction with a user can be, for example, a display of information to the user and a keyboard and a pointing device (e.g., a mouse or a trackball) by which the user can provide input to the computer (e.g., interact with a user interface element). Other kinds of devices can be used to provide for interaction with a user. Other devices can be, for example, feedback provided to the user in any form of sensory feedback (e.g., visual feedback, auditory feedback, or tactile feedback). Input from the user can be, for example, received in any form, including acoustic, speech, and/or tactile input.

The computing device can include, for example, a computer, a computer with a browser device, a telephone, an IP phone, a mobile device (e.g., cellular phone, personal digital assistant (PDA) device, laptop computer, electronic mail device), and/or other communication devices. The computing device can be, for example, one or more computer servers. The computer servers can be, for example, part of a server farm. The browser device includes, for example, a computer (e.g., desktop computer, laptop computer, and tablet) with a World Wide Web browser (e.g., Microsoft® Internet Explorer® available from Microsoft Corporation, Chrome available from Google, Mozilla® Firefox available from Mozilla Corporation, Safari available from Apple). The mobile computing device includes, for example, a personal digital assistant (PDA).

Website and/or web pages can be provided, for example, through a network (e.g., Internet) using a web server. The web server can be, for example, a computer with a server module (e.g., Microsoft® Internet Information Services available from Microsoft Corporation, Apache Web Server available from Apache Software Foundation, Apache Tomcat Web Server available from Apache Software Foundation).

The storage module can be, for example, a random access memory (RAM) module, a read only memory (ROM) module, a computer hard drive, a memory card (e.g., universal serial bus (USB) flash drive, a secure digital (SD) flash card), a floppy disk, and/or any other data storage device. Information stored on a storage module can be maintained, for example, in a database (e.g., relational database system, flat database system) and/or any other logical information storage mechanism.

The above-described techniques can be implemented in a distributed computing system that includes a back-end component. The back-end component can, for example, be a data server, a middleware component, and/or an application server. The above-described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

The above-described networks can be implemented in a packet-based network, a circuit-based network, and/or a combination of a packet-based network and a circuit-based network. Packet-based networks can include, for example, the Internet, a carrier internet protocol (IP) network (e.g., local area network (LAN), wide area network (WAN), campus area network (CAN), metropolitan area network (MAN), home area network (HAN), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, Bluetooth®, code-division multiple access (CDMA) network, time division multiple access (TDMA) network, global system for mobile communications (GSM) network), and/or other circuit-based networks.

Some embodiments of the present invention may be embodied in the form of a system, a method or a computer program product. Similarly, some embodiments may be embodied as hardware, software or a combination of both. Some embodiments may be embodied as a computer program product saved on one or more non-transitory computer readable medium (or media) in the form of computer readable program code embodied thereon. Such non-transitory computer readable medium may include instructions that when executed cause a processor to execute method steps in accordance with embodiments. In some embodiments the instructions stored on the computer readable medium may be in the form of an installed application and in the form of an installation package.

Such instructions may be, for example, loaded by one or more processors and get executed. For example, the computer readable medium may be a non-transitory computer readable storage medium. A non-transitory computer readable storage medium may be, for example, an electronic, optical, magnetic, electromagnetic, infrared, or semiconductor system, apparatus, or device, or any combination thereof.

Computer program code may be written in any suitable programming language. The program code may execute on a single computer system, or on a plurality of computer systems.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

What is claimed is:

1. A method for creating an interpretable model from patient images, the method comprising:
   receiving, via a processor, imaging data of a region of interest of a patient;
   processing, via the processor, the imaging data to provide spatially-localized or temporally-localized information;
   creating, via the processor, a structured representation of the spatially-localized or temporally-localized information that causes at least some of the spatially-localized or temporally-localized information to be indicated as significant spatially-localized or temporally-localized information, wherein creating the structure representation includes:
      i) determining a plurality of cross sections at various location in the region of interest;
      ii) unwrapping each of the plurality of cross sections into two one dimensional vectors to create a plurality of two one dimensional vectors;
      iii) concatenating the plurality of two one dimensional vectors to create the structured representation of the spatially-localized or temporally localized information; and
   using, via the processor, the structured representations for the purpose of training to create the interpretable model, wherein the significant spatially-localized or temporally-localized information contributes to the model inference.

2. The method of claim 1 further comprising using the trained interpretable model for inference.

3. The method of claim 1, wherein the spatially-localized or temporally-localized information includes anatomic information, functional information, tissue characteristics, or any combination thereof.

4. The method of claim 1, wherein the interpretable model output is a quantitative imaging response variable.

5. The method of claim 1, wherein the interpretable model output is a measure of cardiovascular disease status.

6. The method of claim 1, wherein the interpretable model output is a hemodynamic property comprising measure of fractional flow reserve, myocardial blood flow, or any combination thereof.

7. The method of claim 1, wherein the interpretable model output is an event prediction.

8. The method of claim 7, wherein the event prediction is an adverse cardiovascular event or an adverse neurovascular event.

9. The method of claim 1, wherein the interpretable model output is a measure of molecular activity.

10. The method of claim 9, wherein the molecular activity pertains to gene expression or protein levels.

11. The method of claim 1, wherein the significant spatially-localized or temporally-localized information is a tubular structure where proximal function of the tubular structure depends at least in part on distal function of the tubular structure.

12. The method of claim 1, wherein the significant spatially-localized or temporally-localized information couples at least two or more structures in the spatially-localized or temporally-localized information where the interpretable model output is dominated by a subset of those structures.

13. The method of claim 1, wherein the significant spatially-localized or temporally-localized information is contiguous tissues that manifest differing molecular activity based on biological processes.

14. The method of claim 1 further comprising:
generating, via the processor, interpretable labels for unlabeled data based on a function that incorporates mechanistic rationale; and
wherein creating the interpretable model further comprises using, via the processor, the interpretable labels for the purpose of further training the interpretable model, wherein the mechanistic rationale contributes to the model inference.

15. The method of claim 14, wherein the interpretable model output is a quantitative imaging response variable.

16. The method of claim 14, wherein the interpretable model output is a measure of cardiovascular disease status.

17. The method of claim 14, wherein the interpretable model output is a hemodynamic property comprising measure of fractional flow reserve, myocardial blood flow, or any combination thereof.

18. The method of claim 14, wherein the interpretable model output is an event prediction.

19. The method of claim 18, wherein the event prediction is an adverse cardiovascular event or an adverse neurovascular event.

20. The method of claim 19, wherein the interpretable model output is a measure of molecular activity.

21. The method of claim 20, wherein the molecular activity pertains to gene expression or protein levels.

22. A system comprising a processor and a non-transient storage medium including processor executable instructions configured to cause the processor to:

receive imaging data of a region of interest of a patient;
process the imaging data to provide spatially-localized or temporally-localized information;
create a structured representation of the spatially-localized or temporally-localized information that causes at least some of the spatially-localized or temporally-localized information to be indicated as significant spatially-localized or temporally-localized information, wherein creating the structure representation includes:
  i) determine a plurality of cross sections at various location in the region of interest;
  ii) unwrap each of the plurality of cross sections into two one dimensional vectors to create a plurality of two one dimensional vectors;
  iii) concatenate the plurality of two one dimensional vectors to create the structured representation of the spatially-localized or temporally localized information; and
use the structured representations for the purpose of training to create an interpretable model, wherein the significant spatially-localized or temporally-localized information contributes to the model inference.

23. The system of claim 22 further comprising using the trained interpretable model for inference.

24. The system of claim 22, wherein the spatially-localized or temporally-localized information includes anatomic information, functional information, tissue characteristics, or any combination thereof.

25. The system of claim 22, wherein the interpretable model output is a quantitative imaging response variable.

26. The system of claim 22 wherein the system comprising a processor executable instructions are further configured to cause the processor to:
generate interpretable labels for unlabeled data based on a function that incorporates mechanistic rationale; and
wherein to create the interpretable model, the processor executable instructions are further configured to cause the processor to use the interpretable labels for the purpose of further training the interpretable model, wherein the mechanistic rationale contributes to the model inference.

27. The system of claim 26, wherein the interpretable model output is a quantitative imaging response variable.

28. The system of claim 26, wherein the interpretable model output is a measure of cardiovascular disease status.

* * * * *